(12) United States Patent
Fiorenza

(10) Patent No.: US 11,079,026 B2
(45) Date of Patent: Aug. 3, 2021

(54) VALVE FOR BYPASS CONDUIT

(71) Applicant: Smart RS Inc., Ottawa (CA)

(72) Inventor: Francesco Fiorenza, Ottawa (CA)

(*) Notice: Subject to any disclaimer, the term of this patent is extended or adjusted under 35 U.S.C. 154(b) by 0 days.

(21) Appl. No.: 16/504,007

(22) Filed: Jul. 5, 2019

(65) Prior Publication Data
US 2020/0011438 A1 Jan. 9, 2020

(30) Foreign Application Priority Data
Jul. 5, 2018 (CA) .................................. 3010479

(51) Int. Cl.
| F16K 11/074 | (2006.01) |
| F16K 1/20 | (2006.01) |
| F16K 11/052 | (2006.01) |
| F16K 15/03 | (2006.01) |
| A61M 16/20 | (2006.01) |

(52) U.S. Cl.
CPC ....... *F16K 11/0743* (2013.01); *A61M 16/208* (2013.01); *F16K 1/205* (2013.01); *F16K 1/2014* (2013.01); *F16K 11/052* (2013.01); *F16K 15/03* (2013.01)

(58) Field of Classification Search
CPC ......... Y10T 137/2567; Y10T 137/2602; Y10T 137/7891; Y10T 137/86815; Y10T 137/87812; F16K 1/205; F16K 1/2014; F16K 11/052; F16K 11/0743; F16K 15/03
USPC ................ 137/112, 115.12, 625.4, 855, 875; 251/298, 299, 300, 301, 302, 303
See application file for complete search history.

(56) References Cited

U.S. PATENT DOCUMENTS

| 113,829 | A | * | 4/1871 | Allen | F04D 9/005 137/115.06 |
| 1,543,410 | A | * | 6/1925 | Williams | F16K 1/2078 137/629 |
| 1,725,428 | A | * | 8/1929 | Tilden | F16K 15/03 137/527.8 |
| 2,017,033 | A | * | 10/1935 | McGuffin | F16K 15/03 137/513 |
| 2,161,813 | A | * | 6/1939 | Groeniger | E03C 1/108 137/218 |
| 2,214,736 | A | * | 9/1940 | Carmichael | B65G 53/30 406/120 |
| 2,274,776 | A | * | 3/1942 | Cull | F16K 1/2007 251/280 |

(Continued)

*Primary Examiner* — Willliam M McCalister
(74) *Attorney, Agent, or Firm* — US IP Attorneys, P.C.; Timothy Marc Shropshire

(57) ABSTRACT

The present disclosure provides a valve for a respiratory bypass conduit, the valve further comprised of an inner frame that provides rigidity to a flexible outer seal. The inner frame has guiding flanges to guide the valve within he conduit, and a hinge portion to be secured within a slot of the conduit. Together, the hinge and the guiding flanged help the valve move from a first position to a second position. The present disclosure also provides for a method of assembling the valve for respiratory bypass conduit, whereby the inner frame is aligned with and inserted into the outer seal until a peripheral gap of the outer seal substantially houses the inner frame and an inner periphery of the inner frame surrounds a recessed portion of the outer seal to secure the outer seal in the correct orientation relative to the inner frame.

5 Claims, 6 Drawing Sheets

(56) References Cited

U.S. PATENT DOCUMENTS

| | | | | |
|---|---|---|---|---|
| 2,415,466 A * | 2/1947 | Curtis | F16K 11/166 | 137/607 |
| 2,533,921 A * | 12/1950 | Dahl | F16K 1/2021 | 251/142 |
| 2,534,942 A * | 12/1950 | Barling | F16K 1/205 | 4/387 |
| 2,644,479 A * | 7/1953 | Rowley | F16K 1/205 | 137/312 |
| 2,667,934 A * | 2/1954 | Rowley | F16K 1/205 | 169/20 |
| 2,851,286 A * | 9/1958 | Bishop | F16K 1/2014 | 137/359 |
| 2,908,286 A * | 10/1959 | Hallstrom | A47L 5/38 | 137/522 |
| 2,935,291 A * | 5/1960 | Stelzer | F16K 1/205 | 251/263 |
| 3,354,909 A * | 11/1967 | Ake Wallgren | F16K 1/205 | 137/877 |
| 3,705,602 A * | 12/1972 | Nordin | F16K 11/052 | 137/512 |
| 4,043,452 A * | 8/1977 | Ross | F16B 21/186 | 206/343 |
| 4,071,040 A * | 1/1978 | Moriarty | H04M 1/03 | 137/199 |
| 4,718,457 A * | 1/1988 | Luger | B65G 53/56 | 137/875 |
| 4,854,342 A * | 8/1989 | Polan | A62C 35/68 | 137/516.29 |
| 5,186,205 A * | 2/1993 | Bachmann | F16K 1/16 | 137/242 |
| 5,199,597 A * | 4/1993 | Gladish | A47G 19/12 | 220/254.9 |
| 5,697,596 A * | 12/1997 | Kremers | F16K 11/052 | 137/875 |
| 5,908,047 A * | 6/1999 | Nakamura | F01N 3/027 | 137/875 |
| 5,913,504 A * | 6/1999 | Nishimura | F16B 21/186 | 251/62 |
| 5,941,270 A * | 8/1999 | Nogle | F16H 61/0276 | 137/112 |
| 7,534,074 B2 * | 5/2009 | Kato | B65G 53/56 | 137/875 |
| 8,251,627 B2 * | 8/2012 | Inoue | F02M 59/44 | 411/517 |
| 9,611,947 B2 * | 4/2017 | Hallisey | F16K 15/033 |
| 10,309,577 B1 * | 6/2019 | Webb | F16L 55/46 |
| 10,605,134 B2 * | 3/2020 | Dominguez | F01N 3/035 |
| 10,711,788 B2 * | 7/2020 | Mayleben | F04D 13/086 |
| 2003/0217775 A1 * | 11/2003 | Cousineau | F01P 7/16 | 137/625.4 |
| 2005/0263732 A1 * | 12/2005 | Kurian | F16K 27/0272 | 251/298 |
| 2006/0096648 A1 * | 5/2006 | Guerrier | F16K 11/052 | 137/875 |
| 2009/0014674 A1 * | 1/2009 | Grissom | F16K 11/052 | 251/298 |
| 2012/0061601 A1 * | 3/2012 | Marocchini | F16K 11/052 | 251/301 |
| 2014/0144127 A1 * | 5/2014 | Diehl | F16K 11/052 | 60/324 |
| 2019/0383401 A1 * | 12/2019 | Zlatintsis | A62C 35/68 |
| 2020/0011438 A1 * | 1/2020 | Fiorenza | F16K 1/205 |

* cited by examiner

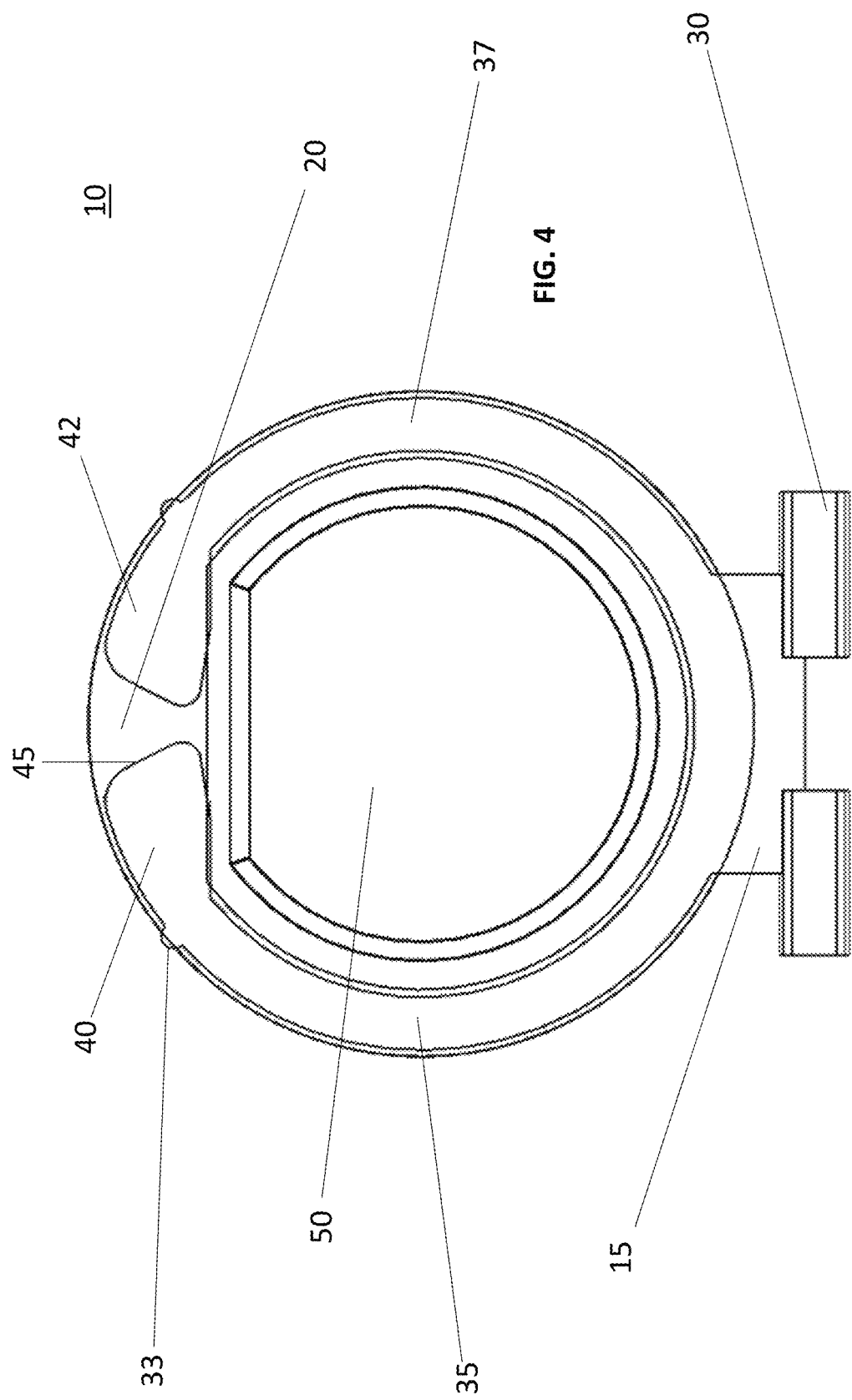

VALVE FOR BYPASS CONDUIT

FIELD

The invention relates to the field of bypass conduits, and more specifically to improved valves for respiratory bypass conduits.

SUMMARY

In an aspect, the present disclosure provides a valve for a bypass conduit, the seal comprising a rigid inner frame having an opening at a front end and a hinge at a rear end; and, a flexible outer seal connected to the inner frame, the flexible outer seal defining a peripheral gap to substantially house the inner frame, wherein the valve is movable from a first position to a second position on the bypass conduit.

In another aspect, the present disclosure provides a method of assembling a valve for a bypass conduit, the steps comprising aligning a recessed portion of the outer seal with an inner periphery of the inner frame; inserting first and second connectors of the inner frame into a peripheral gap of the outer seal; making contact with sloping front faces of the inner frame to an inner wall of the recessed portion to facilitate insertion of the inner frame into the outer seal; and, continuing to insert the inner frame within the outer seal until the peripheral gap of the outer seal substantially houses the inner frame and an inner periphery of the inner frame surrounds the recessed portion and therefore secures the outer seal in the correct orientation relative to the inner frame.

BRIEF DESCRIPTION OF THE DRAWINGS

The following figures serve to illustrate various embodiments of features of the disclosure. These figures are illustrative and are not intended to be limiting.

FIG. 4 is a top view of the valve according to an embodiment of the present disclosure;

DETAILED DESCRIPTION

The following embodiments are merely illustrative and are not intended to be limiting. It will be appreciated that various modifications and/or alterations to the embodiments described herein may be made without departing from the disclosure and any modifications and/or alterations are within the scope of the contemplated disclosure.

Figure 1:
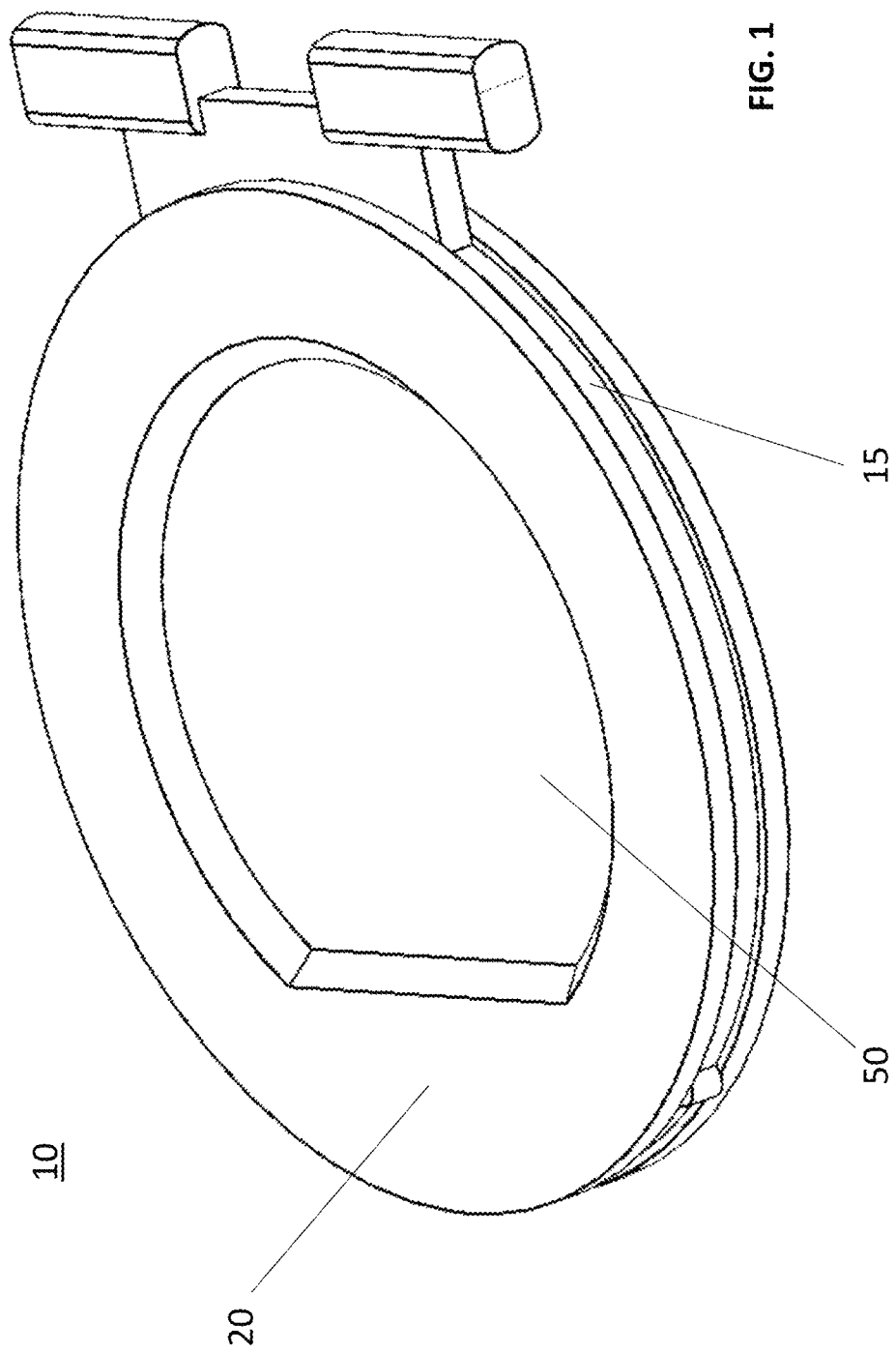
FIG. 1 is a perspective view of a valve according to an embodiment of the present disclosure.
Figure 2:
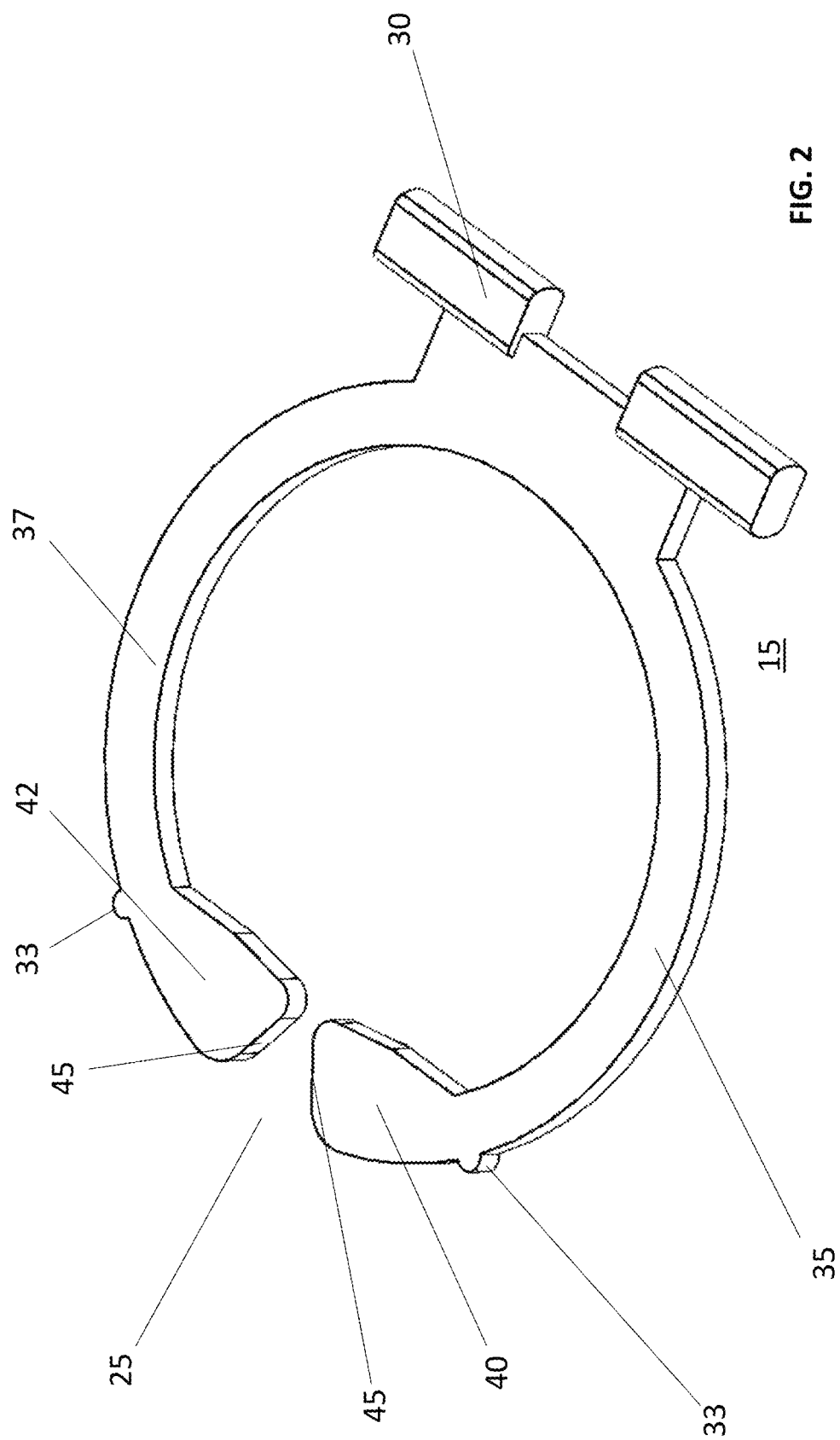
FIG. 2 is a perspective view of an inner frame of the valve according to an embodiment of the present disclosure.
Figure 3:
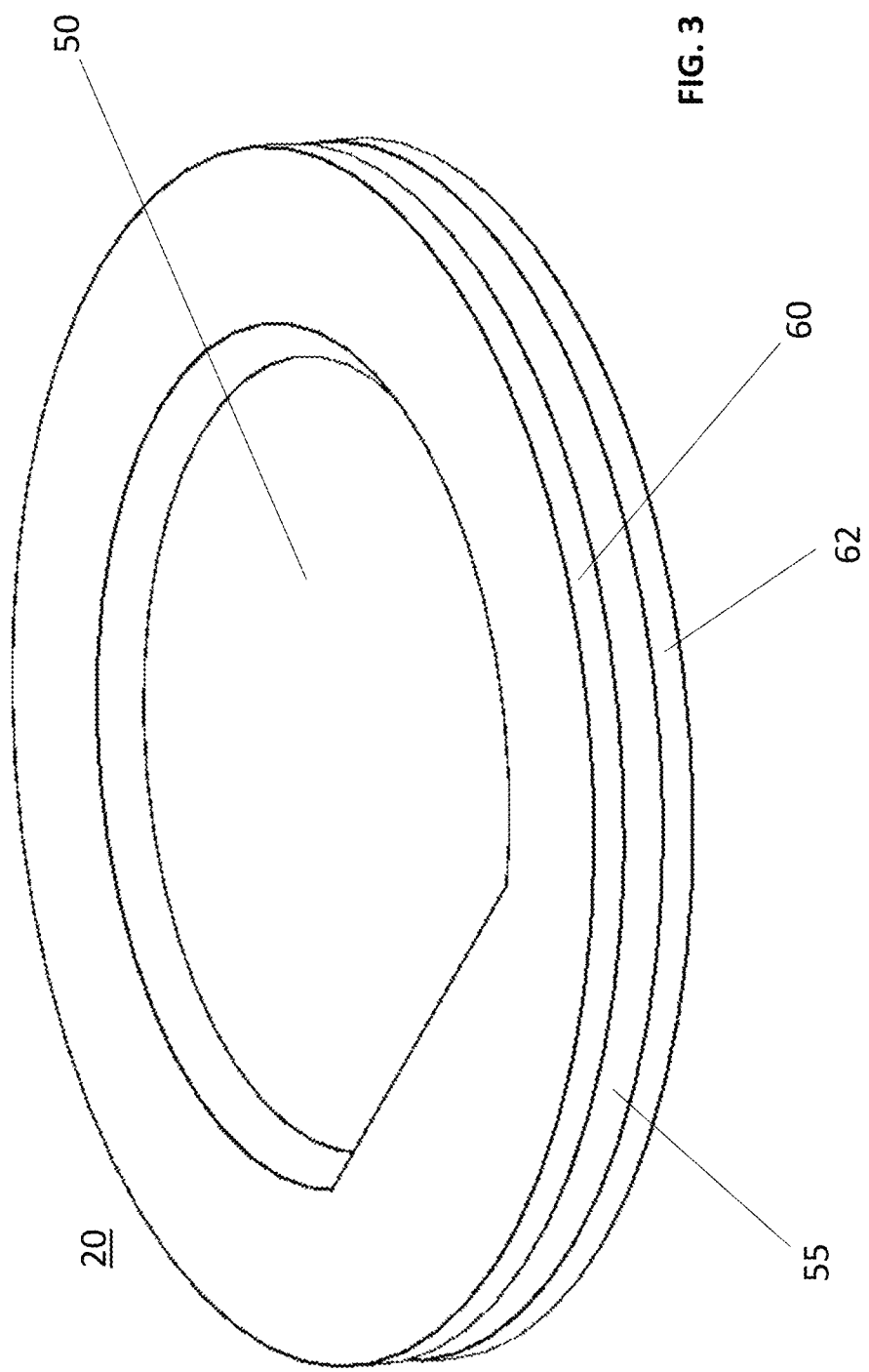
FIG. 3 is a perspective view of a flexible outer seal of the valve according to an embodiment of the present disclosure.

With reference to FIGS. 1, 2 and 3 and according to an embodiment of the present disclosure, a valve 10 for use in a respiratory bypass conduit is disclosed. The valve 10 is comprised of a rigid inner frame 15 that provides rigidity to a flexible outer seal 20. The inner frame 15 is defined by a front end having an opening 25, and a rear end having a hinge 30. The hinge 30 is designed to mate with a corresponding slot (not shown) of the bypass conduit to move the valve 10 from a first position to a second position. The first position is the area where the valve 10 covers an aperture in a first portion of the valve conduit, and the second position is the area where the valve 10 covers another aperture in a second portion of the valve conduit. The inner frame is further comprised of two guiding flanges 33 that make contact with an inner portion of a conduit (not shown) to keep the valve 10 aligned and moving between the first and second positions. Indeed, the guiding flanges 33 create the requisite friction to maintain the correct pivoting of the valve 10. The inner frame 15 is also comprised of first and second arms 35, 37 that are substantially circularly shaped. First and second arms 35, 37 terminate in first and second connectors 40, 42, respectively. First and second connectors 40, 42 each have a sloping front face 45, the sloping front face 45 angled to facilitate receiving the outer seal 20 during the assembly of the valve 10. The assembly of the valve 10 will be further disclosed below. The inner periphery of the inner frame 15 has a shape that corresponds to a recessed portion 50 of the outer seal 20. Indeed, the inner periphery of the inner frame 15 surrounds and encloses a recessed portion 50 of the outer seal 20 such that the outer seal 20 stays in the same position and orientation relative to the inner frame 15. The recessed portion 50 has a first circular side and a second straight side, as specifically shown in FIG. 3. The outer seal 20 is further comprised of a peripheral gap 55 to substantially house the first and second arms 35, 37 and first and second connectors 40, 42 of the inner frame 15. The peripheral gap 55 is defined as the space surrounding the recessed portion 50 of the outer seal 20 and in between upper and lower flaps 60, 62 of the outer seal 20.

With reference to FIG. 4 and according to an embodiment of the present disclosure, the outer seal 20 is shown substantially surrounding the inner frame 15. The hinge 30 is shown protruding from the outer seal 20 to contact a slot (not shown) of the bypass conduit. The guiding flanges 33 are also shown protruding from the periphery of the outer seal 20 to guide the valve 10 from the first position to the second position in the bypass conduit. As shown, the recessed portion 50 of the seal 20 is surrounded and enclosed by the inner periphery of the inner frame 15. The first and second arms 35, 37 of the inner frame 15 are contained within the peripheral gap (not shown) of the outer seal 20. To assemble the valve 10, the outer seal 20 is positioned proximate the front end of the inner frame 15, and the shape of the recessed portion 50 of the outer seal 20 is oriented in the same manner as the shape of the inner periphery of the inner frame 15. The first and second connectors 40, 42 of the inner frame 15 are then inserted into the peripheral gap (not shown) of the outer seal 20 until the sloping front faces 45 of the first and second connectors 40, 42 make contact with an inner wall (not shown) of the recessed portion 50. The sloping front faces 45 help facilitate the continued insertion of the recessed portion 50 of the outer seal 20 into the opening 20 of the inner frame 15. Indeed, the recessed portion 50 of the outer seal 20 compresses to fit through the opening 20 of the inner frame 15 until the recessed portion 50 has been completely inserted through the opening 20. At this point, the inner periphery of the inner frame 15 surrounds the recessed portion 50 and therefore secures the outer seal 20 in the correct orientation relative to the inner frame 15. In the assembled state of the valve 10, the peripheral gap 55 of the outer seal 20 substantially houses the inner frame 15.

Figure 5A:
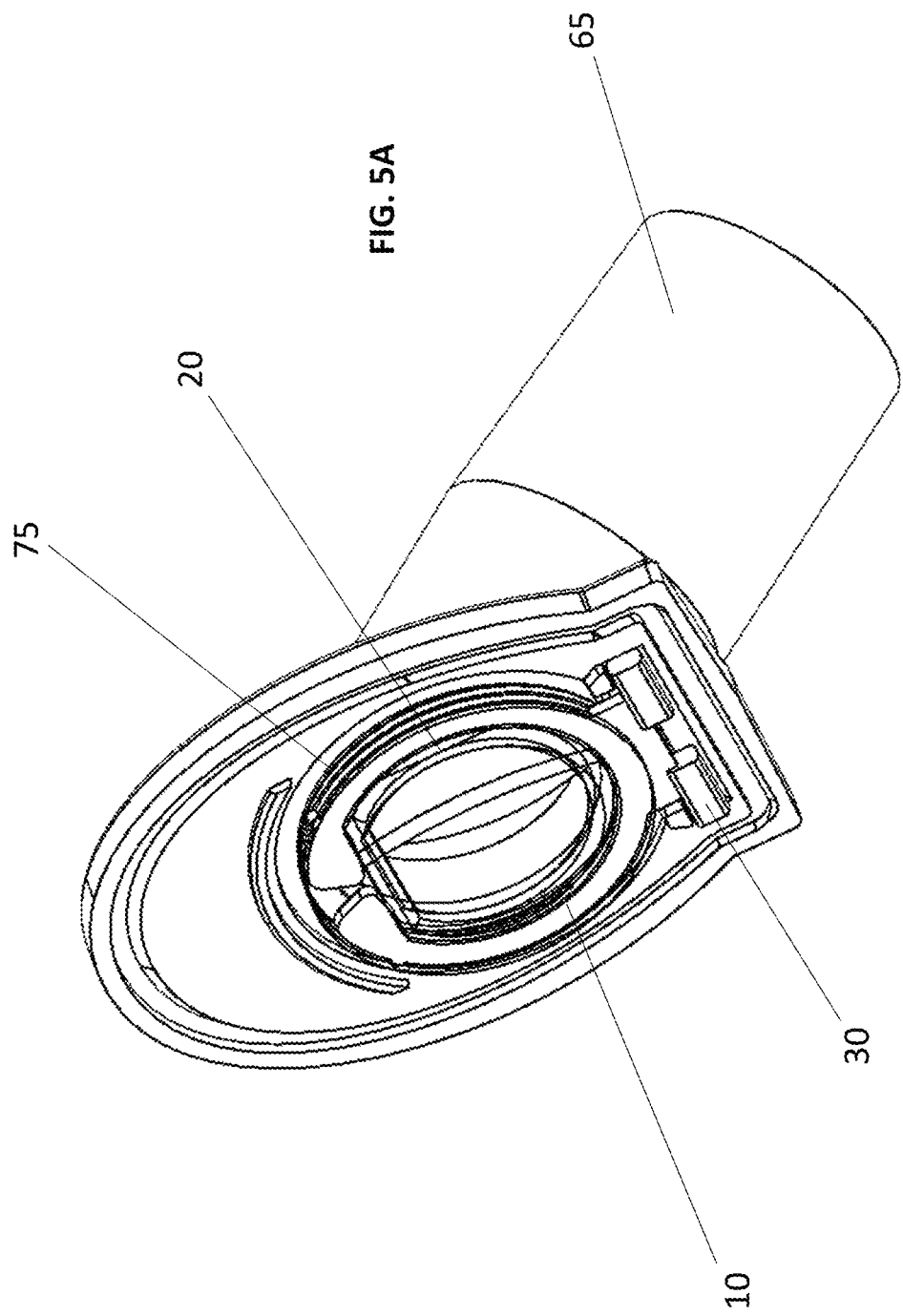
FIG. 5A is a perspective cross-sectional view of the valve within a portion of a bypass conduit according to an embodiment of the present disclosure; and, FIG. 5B is a front cross-sectional view of the valve within the bypass conduit according to an embodiment of the present disclosure.
Figure 5B:
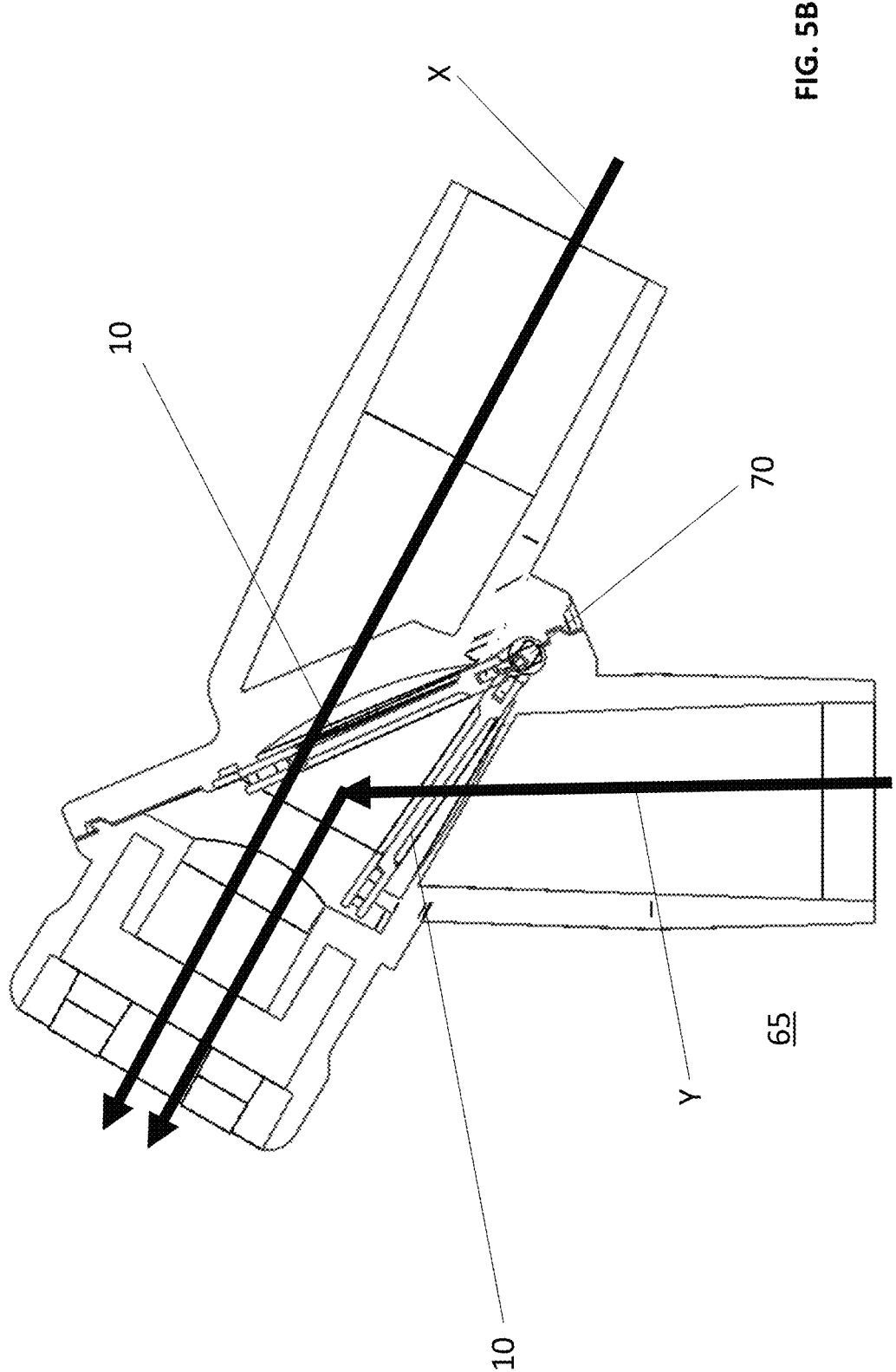

With reference to FIGS. 5A and 5B and according to an embodiment of the present disclosure, the valve 10 is shown positioned in a bypass conduit 65. Indeed, the hinge 30 of the valve 10 is secured into the slot 70 of the bypass conduit 60. With specific reference to FIG. 5B, the valve 10 is shown moving from a first position to a second position within the bypass conduit 65. A worker skilled in the art would appreciate that when the valve 10 is in the first position, air can flow through the bypass conduit 65 in direction X, while when the valve is in the second position, air can flow through the bypass conduit in direction Y. The bypass conduit 65 is further comprised of a raised ridge 75 to improve the seal between the outer seal 20 and the bypass conduit 65.

Many modifications of the embodiments described herein as well as other embodiments may be evident to a person skilled in the art having the benefit of the teachings presented in the foregoing description and associated drawings. It is understood that these modifications and additional embodiments are captured within the scope of the contemplated disclosure which is not to be limited to the specific embodiment disclosed.

I claim:

1. A valve for a bypass conduit, the valve comprising:
    a rigid frame comprising:
        a first arm and a second arm, each of which extend forward from a rear hinge portion of the frame, wherein an area between a first end and a second end of the first arm and the second arm is open;
        a first guiding flange extending radially from the first arm; and
        a second guiding flange extending radially from the second arm; and
    a flexible seal comprising an outer peripheral gap, said peripheral gap being configured to receive and contain an entire length and width of the first arm and the second arm therewithin,
    wherein the first arm and the second arm are configured to seat within the peripheral gap to removably engage the frame with the seal,
    wherein the first guiding flange and the second guiding flange are configured to extend radially beyond an outer edge of the peripheral gap when the first arm and the second arm are seated within the peripheral gap,
    wherein the rear hinge portion of the frame is configured to hingedly engage the bypass conduit,
    wherein the valve is configured to transition from a first position to a second position on the bypass conduit,
    wherein the first guiding flange and the second guiding flange are configured to contact the bypass conduit to maintain alignment between the bypass conduit and the valve as the valve transitions from the first position to the second position.

2. The valve of claim 1, wherein the first arm and the second arm terminate in a first connector and a second connector, respectively, wherein a front face of each of the first connector and the second connector is angled to facilitate engagement of the frame with the seal.

3. The valve of claim 1, wherein the seal comprises a central recessed portion.

4. The valve of claim 3, wherein a shape of the recessed portion comprises a circular rear segment truncated by a straight front segment.

5. A method of assembling a valve for a bypass conduit comprising:
    aligning a recessed portion of a flexible seal with an inner periphery of a rigid frame;
    inserting a first connector portion and a second connector portion of a first arm and a second arm, respectively, of the frame into a peripheral gap of the seal;
    making contact between angled front faces of the frame and a inner wall of the recessed portion to facilitate engagement of the frame with the seal; and
    inserting a remaining length of the first arm and the second arm into the peripheral gap,
    wherein the peripheral gap is configured to receive and contain an entire length and width of the first arm and the second arm therewithin,
    wherein, when the first arm and the second arm are fully inserted, an inner periphery of the frame is configured to restrict movement of the recessed portion to secure the seal in the correct orientation relative to the frame.

* * * * *